United States Patent [19]

Kawawa et al.

[11] 4,141,812
[45] Feb. 27, 1979

[54] OXYGEN SENSORS

[75] Inventors: Takao Kawawa; Ryoichiro Imai; Hisami Tokunaga, all of Fukuyama; Yutaka Nakano, Funabashi; Naoaki Sasaki, Tokyo, all of Japan

[73] Assignees: Nippon Kokan Kabushiki Kaisha, Tokyo; Osaka Oxygen Industries, Ltd., Osaka, both of Japan

[21] Appl. No.: 882,633

[22] Filed: Mar. 2, 1978

[30] Foreign Application Priority Data

Mar. 2, 1977 [JP] Japan .............................. 52-23814[U]

[51] Int. Cl.² ...................... G01N 27/30; G01N 27/58
[52] U.S. Cl. ................................................. 204/195 S
[58] Field of Search .......................... 204/195 S, 1 S; 23/254 E; 123/119 E; 324/29

[56] References Cited

U.S. PATENT DOCUMENTS 3,772,177  11/1973  Rittiger et al. .................. 204/195 S Primary Examiner—G. L. Kaplan
Attorney, Agent, or Firm—Fleit & Jacobson

[57] ABSTRACT

There is disclosed an improved electrical contact structure between a solid electrolyte galvanic cell and a powder reference material for detecting the oxygen content of molten metals. The solid electrolyte galvanic cell has a portion embedded in the powder reference material and the portion is irregularly shaped so as to increase the contact area and strength of the joint between the embedded portion and the powder reference material.

8 Claims, 19 Drawing Figures

FIG. 11 FIG. 10
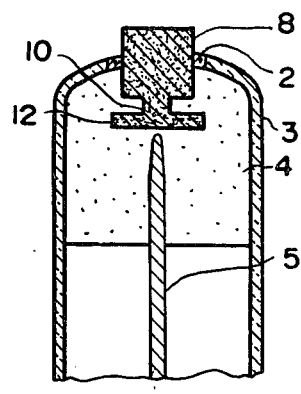
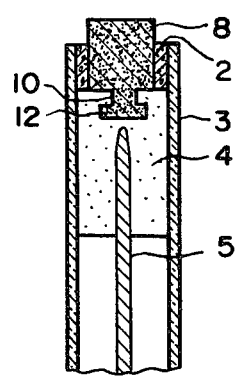
FIG. 12 FIG. 13 FIG. 14
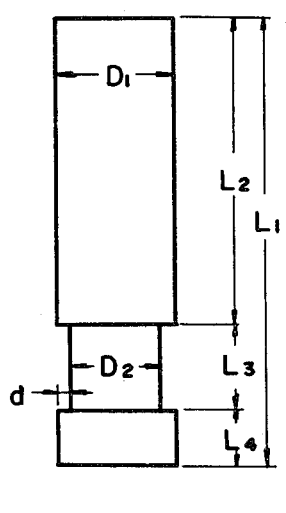
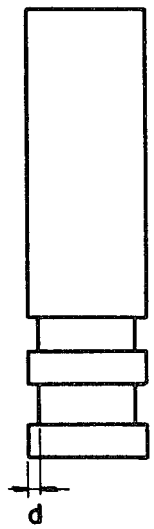
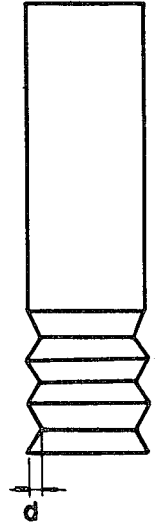

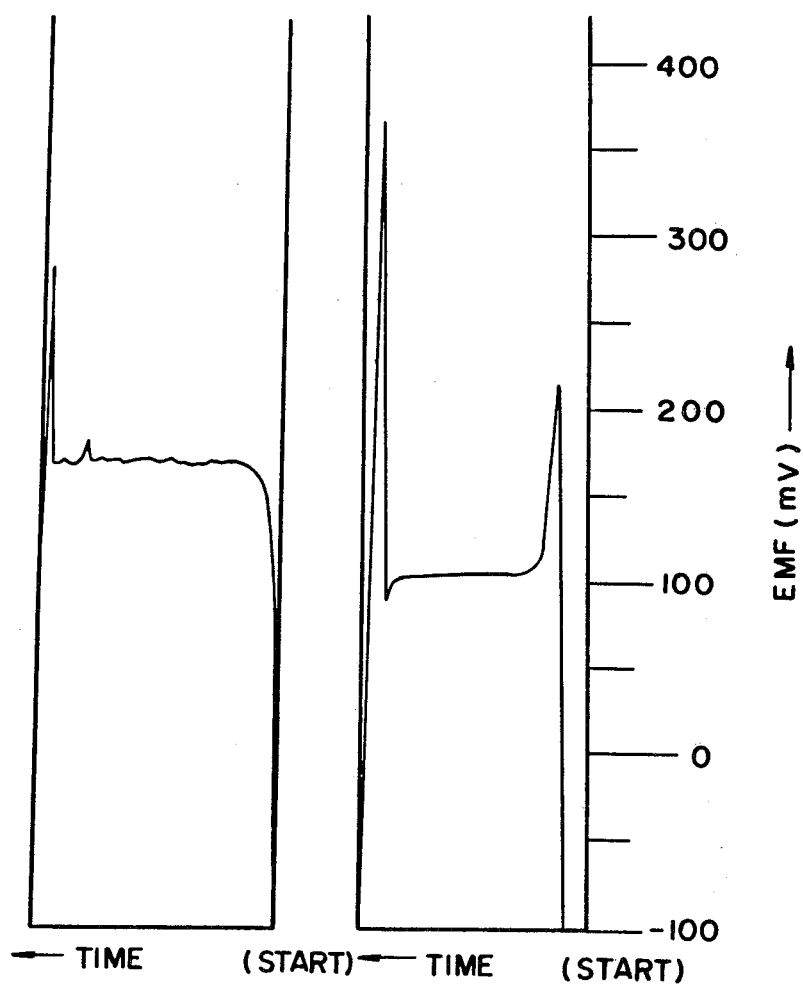

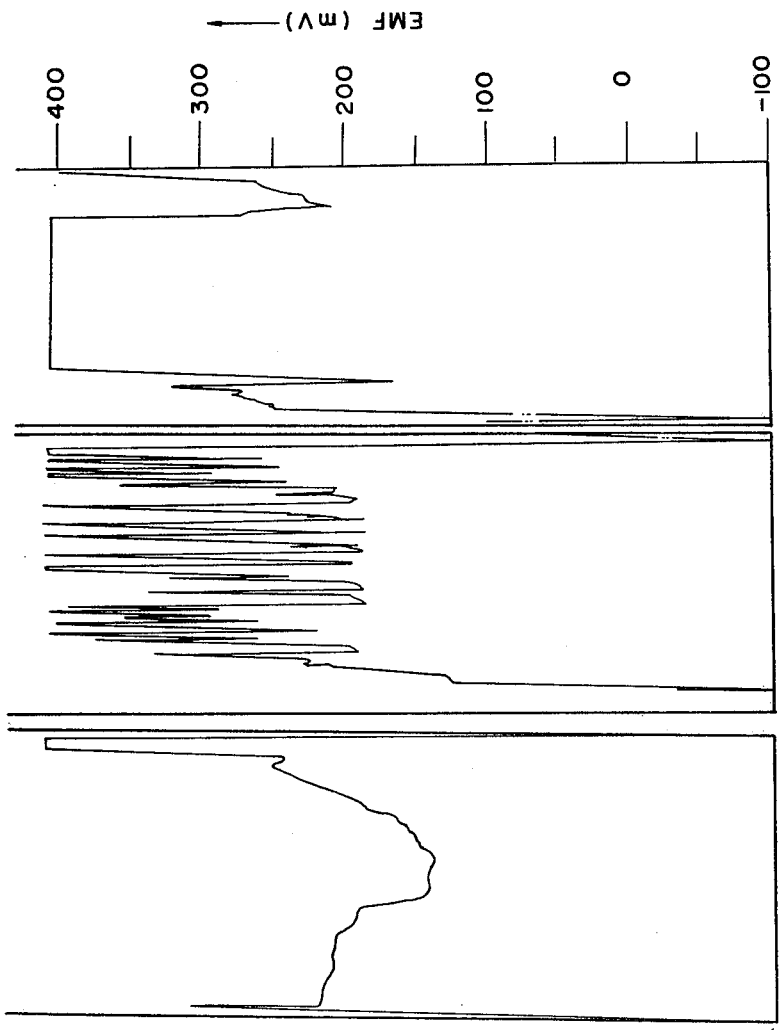

OXYGEN SENSORS

BACKGROUND OF THE INVENTION

The present invention relates to oxygen sensors for measuring the oxygen content of molten metals, particularly molten iron, and more particularly the invention relates to improvements in the electrical contact structure between the solid electrolyte galvanic cell and the powder reference material in such oxygen sensors.

While research works and development of devices for measuring the oxygen content of molten iron have been carried out by many different companies all over the world, all of these devices are based on the processes which are basically similar in nature. Particularly, the solid electrolyte galvanic cells (e.g., $ZrO_2$-$Ca_2$, $ZrO_2$-$Y_2O_3$ or $ZrO_2$-$MgO$) which are used as ionic conductors in such devices are for the most part formed into a simple cylindrical shape, and the contact structure between the solid electrolyte galvanic cell and a powder reference material (such as, mixed powder of Cr and $Cr_2O_3$ or mixed powder of Mo and $MoO_2$) is in the form of a simple surface-to-surface contact.

The typical shape and mounting of the solid electrolyte galvanic cells in the known oxygen sensors are shown in FIG. 1. In the Figure, a cylindrical solid electrolyte galvanic cell 1 is mounted inside a quartz tube 3 by fusion or cementing (the portion indicated at numeral 2), and the solid electrolyte galvanic cell 1 makes, within the quartz tube 3, a surface-to-surface contact with a powder reference material 4 contained in the quartz tube 3 below the solid electrolyte galvanic cell 1. If the device in this condition is immersed into molten iron from the direction of an arrow 7, an electromotive force corresponding to the partial pressure of oxygen in the molten iron is produced across the solid electrolyte galvnic cell 1 or between the molten iron and the powder reference material 4 and delivered by way of electrode lead wires 5 and 6, and consequently the concentration of oxygen dissolved in the molten iron can be determined by measuring the thus delivered electromotive force.

When the oxygen sensor of the type shown in FIG. 1 is immersed into molten iron, an apparent contraction is caused in the powder reference material 4 upon occurrence of its sintering phenomenon due to high temperature, and the solid electrolyte galvanic cell 1 and the powder reference material 4 contacting each other in surface-to-surface relation are separated from each other, thus causing contact failure, causing electrically deflective conduction with the resulting increase in electric resistance, making it impossible to satisfactorily measure the generated electromotive force and thereby deteriorating the resulting emf curve which will be described later and causing the measurement to end in failure.

To overcome these deficiencies, the prior art devices of the type disclosed for example by the invention of U.S. Pat. No. 3,772,177 have been proposed. In the prior art device of this type, as shown in FIG. 2, that portion of an electrolyte galvanic cell 1 contacting a reference material 4 has the shape of a frustrum, and this frustrum 9 is embedded in and surrounded by the reference material 4. Also in this case, however, when the reference material 4 contracts, the reference material 4 slidingly contracts in the direction of the arrow, thus in most instances causing the electrolyte galvanic cell 1 and the reference material 4 to separate from each other and thereby causing the measurement to end in failure. The results of the actual tests made with this prior art device showed that the measured emf curves were for the most part unsatisfactory as shown in FIGS. 17, 18 and 19 of the accompanying drawings. Also the results of the tests made by modifying the shape of the frustrum 9, namely, by forming that portion of the electrolyte galvanic cell contacting the reference material into a conical shape entirely and embedding this conical portion in the reference material, showed about the same results as obtained with the frustrum and the rate of success in measurements was not improved considerably.

SUMMARY OF THE INVENTION

In accordance with the present invention, in an oxygen sensor the shape of a portion of a solid electrolyte galvanic cell embedded in a reference material is modified, thus maintaining the desired electric contact between the solid electrolyte galvanic cell and the reference material during measurements and thereby ensuring positive and accurate measurement of the oxygen content of molten metals.

It is therefore an object of the present invention to provide an oxygen sensor having an improved contact structure which prevents the occurrence of electrical contact failure between a solid electrolyte galvanic cell and a powder reference material due to the sintering of the latter, thereby improving the rate of success in measurements.

It is another object of this invention to provide an improved oxygen sensor in which that portion of a solid electrolyte galvanic cell contacting a powder reference material is irregularly shaped, thereby ensuring improved electrical contact and holding properties.

It is still another object of the invention to provide an oxygen sensor in which the portion of the solid electrolyte galvanic cell contacting the powder reference material consists of a small-diameter portion and a large-diameter portion which are connected to the cylindrical body portion.

It is still another object of the invention to provide an oxygen sensor in which the portion of the solid electrolyte galvanic cell contacting the powder reference material consists of a series of alternate small-diameter and large-diameter portions which are connected to the cylindrical body portion.

These and other objects, advantages, features and uses will become more apparent as the description proceeds, when considered with the accompanying drawings.

BRIEF DESCRIPTION OF THE DRAWINGS

FIG. 10 is a sectional view showing the consturction of the oxygen sensor of this invention using the solid electrolyte galvanic cell shown in FIG. 5.

FIG. 11 is a sectional view showing another construction of the oxygen sensor of this invention using the solid electrolyte galvanic cell shown in FIG. 6.

FIG. 12 is an explanatory diagram showing the dimension of the various parts of one solid electrolyte galvanic cell used in the oxygen sensor of this invention.

FIG. 13 is an explanatory diagram showing the depth of the depressions formed in the contacting portion of another solid electrolyte galvanic cell used in the oxygen sensor of this invention.

FIG. 14 is an explanatory diagram showing the depth of the depressions formed in the contacting portion of still another solid electrolyte galvanic cell used in the oxygen sensor of this invention.

FIG. 15 is a graph showing the emf curve obtained when the oxygen content of rimmed steel was successively measured with the oxygen sensor of this invention.

FIG. 16 is a graph showing the emf curve obtained when the oxygen content of semi-killed steel was successively measured with the oxygen sensor of this invention.

FIG. 17 is a graph showing the unstable emf curve produced by the unsuccessful measurement made with the prior art oxygen sensor.

FIG. 18 is a graph showing the emf curve with hunting which was produced by the unsuccessful measurement made by the prior art oxygen sensor.

FIG. 19 is a graph showing the emf curve with a scaleover, which was produced by the unsuccessful measurement made with the prior art oxygen sensor.

DESCRIPTION OF THE PREFERRED EMBODIMENTS

Figure 5:
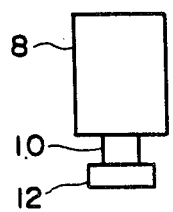
FIG. 5 is a front view showing still another embodiment of the solid electrolyte galvanic cell used in the oxygen sensor of this invention.
Figure 7:
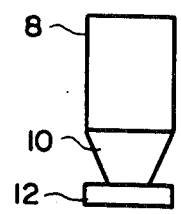
FIG. 7 is a front view showing still another embodiment of the solid electrolyte galvanic cell used in the oxygen sensor of this invention.
Figure 8:
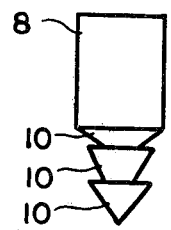
FIG. 8 is a front view showing still another embodiment of the solid electrolyte galvanic cell used in the oxygen sensor of this invention.
Figure 9:
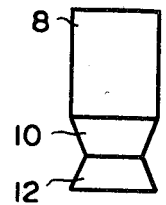
FIG. 9 is a front view showing still another embodiment of the solid electrolyte galvanic cell used in the oxygen sensor of this invention.

The solid electrolyte galvanic cell used in an oxygen sensor according to the invention provides the features that the portion of the solid electrolyte galvanic cell contacting the powder reference material is irregularly shaped to prevent the occurrence of sliding between the solid electrolyte galvanic call and the powder reference material. In other words, in FIG. 3 the contacting portion comprises a small-diameter portion 10 and a large-diameter portion 12 connected to the small-diameter portion 10 and including a conical head of the same outer diameter as a body portion 8; FIG. 4 shows the contacting portion of the same type shown in FIG. 3 except that the large-diameter portion has a spherical head; FIG. 5 shows the contacting portion in which the large-diameter portion 12 connected to the small-diameter portion 10 is smaller in outer diameter than the body, and in FIG. 6 the large-diameter portion 12 is greater in outer diameter than the body portion. FIG. 7 shows a modification of FIG. 3, in which the small-diameter portion 10 is formed into a conical shape and connected to the large-diameter portion 12, FIG. 8 shows the construction including a series of conically drawn small-diameter portions 10 providing a plurality of alternate projections and depressions, and FIG. 9 shows the construction in which the small-diameter portion 10 is drawn into a conical shape relative to the body 8 and the large-diameter portion 12. FIGS. 10 and 11 show exemplary manners of mounting the solid electrolyte galvanic cell of this invention having such irregularly shaped contacting portion.

Figure 6:
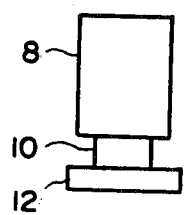
FIG. 6 is a front view showing still another embodiment of the solid electrolyte galvanic cell used in the oxygen sensor of this invention.

FIG. 10 shows an embodiment in which the solid electrolyte galvanic cell of FIG. 5 is mounted, and FIG. 11 shows another embodiment in which the solid electrolyte galvanic cell of FIG. 6 is mounted. More specifically, the powder reference material 4 fittingly encloses the irregularly shaped portion of the solid electrolyte galvanic cell 8 comprising the large-diameter portion 12 and the small-diameter portion 10. As a result, when the oxygen sensor is immersed into molten iron so that the powder reference material 4 sinters, the powder reference material 4 contracts while enclosing the irregularly shaped portion in such a manner that the powder reference material 4 enters into the depression of the irregularly shaped portion and the irregularly shaped portion serves as a sliding preventive stop. This has the effect of preventing the solid electrolyte galvanic cell 8 and the powder reference material 4 from separating from each other and diminishing the electrical contact therebetween and thereby ensuring positive and accurate measurement of the generated electromotive force and achieving a high rate of measuring success.

With the mounting structure shown in FIG. 11, the portion of a quartz tube 3 near a fused portion 2 is curved to be drawn. This is designed to ensure that the powder reference material 4 can enclose the solid electrolyte galvanic cell 8 more extensively. In addition, by virtue of the fact that the large-diameter portion 12 of the solid electrolyte galvanic cell 8 is projected with an outer diameter greater than the body portion, the contact area between the solid electrolyte galvanic cell 8 and the power reference material 4 is increased. By virtue of the mounting structure which ensures an increased contact area, the mounting structure of FIG. 11 can ensure more satisfactory measurement results than that of FIG. 10 and thus the embodiment of FIG. 11 can be said the most suitable one.

The shape of the irregular contacting portion which is so termed in this application, is not limited to those shown in the drawings, and it is of course possible to use any shape to suit the intended use and the desired functions and effects.

Further, the curvature of the quartz tube in FIG. 11 is such that the inner diameter of the quartz tube 3 is made greater than the outer diameter of the solid electrolyte galvanic cell 8 to provide a sufficient space for containing and enclosing the powder reference material 4 and then the quartz tube 3 is curved by an amount corresponding to the space. Of course, the quartz tube may be bent at right angles. In short, what is important here is to provide a space so as to easily enclose the solid electrolyte galvanic cell 8 with the powder reference material 4 and allow the powder reference material 4 to enter between the solid electrolyte galvanic cell 8 and the quartz tube 3, and preferably the quartz tube 3 is curved for fusing the quartz tube 3 to the solid electrolyte galvanic cell 8. The space between the quartz tube 3 and the solid electrolyte galvanic cell 8 is dependent on the particulate size of the powder reference material. For example, when the particulate size is in the range of 1 to 50 micron, the space of as small as about 0.006 mm is sufficient for filling purposes with the presently available filling techniques and consequently it is only necessary to provide a space width of at least over 0.06 mm. Of course, the space width may be made greater, although it is subject to restrictions imposed by the fusing techniques.

Further, while the depth of the space for introducing the powder reference material is dependent on the size of the solid electrolyte galvanic cell 8, the size of its irregular contacting portion, etc., thus making it impossible to make a sweeping statement, where the solid electrolyte galvanic cell 8 is cylindrical the depth of the space must be equivalent at least to the length of the irregular contacting portion. However, it is desirable that the depth of the space be made as long as possible so as to ensure an improved measuring capacity.

More specifically, the width and depth of the space are respectively selected 0.1 to 1 mm and about 4.5 mm for mounting the solid electrolyte galvanic cells of the shapes shown in FIGS. 5 and 6. While such a large space is not needed from the standpoint of the principle, the use of a practical size is rather proposed in consideration of the fusing operation, manufacture of electrodes, assembling operation, etc., and the size should be as large as possible provided that these conditions are met.

By the way, if the depth of the space exceed 4.5 mm, the contact distance between the electrolyte galvanic cell and the powder reference material increases, and thereby a difference to electromotive force takes place between the upper contacting part and the lower contacting part of the electrolyte galvanic cell, and the electromotive force reduces as an abnormal status. In order to minimize such difference of electromotive force, it is desirable to adjust the depth of the space to 1.5 mm.

On the other hand, the required number of projections and depressions formed in the contacting portion of the solid electrolyte galvanic cell is such that while the desired effect of the invention can be produced by providing at least one irregular section at one place on the circumference of the solid electrolyte galvanic cell contacting the powder reference material, better results can be obtained by increasing the number and consequently it is most desirable to provide a plurality of projections and depressions over the entire circumference of the solid electrolyte galvanic cell. As regards the size of the irregular section, the same effect can be obtained by decreasing the size as the number of the irregular sections is increased and the size of the irregular sections must be increased with decrease in the number.

Now, some specific examples of the irregular sections formed over the entire circumference of the solid electrolyte galvanic cell with be described with reference to FIGS. 12, 13 and 14. It will be seen that that the depth d of the depressions on the solid electrolyte galvanic cells shown in FIGS. 12 to 14 is decreased with increase in the number of the depressions. When the number of depressions is increased, angular depressions are preferred as shown in FIG. 14. The actual measurement tests conducted by using these solid electrolyte galvanic cells showed that quite satisfactory electric contact characteristics could be obtained with all of these solid electrolyte galvanic cells. A comparison of the solid electrolyte galvanic cells shown in FIGS. 12, 13 and 14 has shown that the depth d of each depression can be decreased as the number of the depressions is increased in FIGS. 12, 13 and 14 in this order, and particularly in the case of FIG. 14 using a greater number of depressions, the desired effect can be obtained with the depth d of as small as 0.1 mm. It has also been shown that the desired effect can be produced with d=0.15 mm in the case of FIG. 13.

Although the provision of a single small irregular section will be sufficient for accomplishing the objects of this invention, ideally it is desirable to provide a large number of large depressions. However, in consideration of the actual manufacturing techniques of solid electrolyte galvanic cell, that is, the molding of solid electrolyte galvanic cell involving the process of preparing a split die, introducing into and sintering an electrolyte in the split die and molding the same into a solid electrolyte galvanic cell by a molding press or injection molder, the mounting techniques of solid electrolyte galvanic cell, the assemblying techniques of electrodes, etc., the most preferred shape will be the one shown in FIG. 12 employing the depression having the depth d of about 0.25 mm.

The dimensions of the solid electrolyte galvanic cell of FIG. 12 are as follows.

$D_1 = 2.0 \phi$
$D_2 = 1.5 \phi$
$l_1 = 8.0$ mm
$l_2 = 5.5$ mm
$l_3 = 1.5$ mm
$l_4 = 1.0$ mm The following Table 1 shows, in comparison with the results obtained with the prior art devices, the rates of success in the measurements made with the oxygen sensor of this invention employing the solid electrolyte galvanic cells of the above mentioned shapes. In Table 1, each denominator represents the number of the measurements made and each numerator represents the number of the successful measurements.

Table 1

Figure 1:
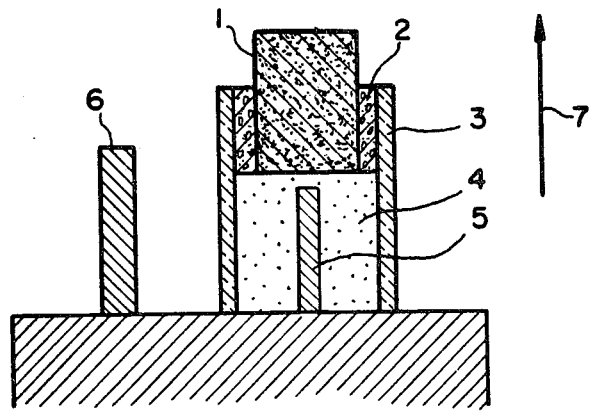
FIG. 1 is a sectional view showing the construction of a known oxygen sensor constituting the prior art for the present invention.
Figure 2:
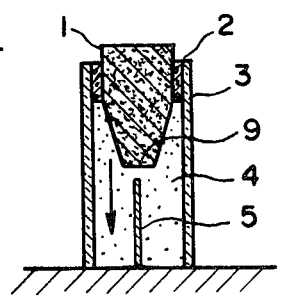
FIG. 2 is a sectional view showing the construction of another known oxygen sensor constituting the prior art for the present invention.
Figure 3:
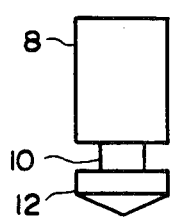
FIG. 3 is a front view showing an embodiment of the solid electrolyte galvanic cell used in an oxygen sensor according to the invention.
Figure 4:
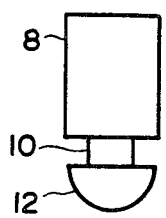
FIG. 4 is a front view showing another embodiment of the solid electrolyte galvanic cell used in the oxygen sensor according to the invention.

| Measuring conditions | | Rate of Successful Measurements (%) | | | |
|---|---|---|---|---|---|
| | | Prior art | | Present invention | |
| Furnace | Type of steel | FIG. 1 | FIG. 2 | FIG. 3 | FIG. 4 |
| Test furnace | 0.03 – 0.30 % C molten steel | $\frac{396}{626} = 63$ | $\frac{7}{10} = 70$ | $\frac{27}{30} = 90$ | $\frac{295}{300} = 98$ |
| | 0.03 – 0.30 % C, 0.05 – 0.30 % Si molten steel | $\frac{299}{412} = 73$ | $\frac{7}{10} = 70$ | $\frac{27}{30} = 90$ | $\frac{230}{230} = 100$ |
| Ladle (250 t) | Rimmed steel | $\frac{181}{301} = 60$ | $\frac{7}{10} = 70$ | $\frac{8}{10} = 80$ | $\frac{192}{200} = 96$ |
| | Semi-killed steel | $\frac{198}{301} = 66$ | $\frac{6}{10} = 60$ | $\frac{9}{10} = 90$ | $\frac{582}{601} = 97$ |
| C.C. | Semi-killed steel | $\frac{138}{220} = 63$ | $\frac{6}{10} = 60$ | $\frac{8}{10} = 80$ | $\frac{140}{150} = 93$ |

Table 1-continued

| Measuring conditions | | Rate of Successful Measurements (%) | | | |
| --- | --- | --- | --- | --- | --- |
| | | Prior art | | Present invention | |
| Furnace | Type of steel | FIG. 1 | FIG. 2 | FIG. 3 | FIG. 4 |
| tundish | Killed steel | $\frac{61}{100} = 61$ | $\frac{7}{10} = 70$ | $\frac{9}{10} = 90$ | $\frac{47}{50} = 94$ |
| Mold | Rimmed steel | $\frac{146}{250} = 58$ | $\frac{6}{10} = 60$ | $\frac{17}{20} = 85$ | $\frac{379}{400} = 95$ |
| | Semi-killed steel | $\frac{125}{200} = 63$ | $\frac{7}{10} = 70$ | $\frac{17}{20} = 85$ | $\frac{189}{200} = 95$ |

As will be seen from Table 1, the rates of success obtained with the devices of this invention are extremely high as compared with those of the prior art devices.

In Table 1, the determination of the successful and unsuccessful measurements was made on the basis that the successful measurement is one in which the recorded emf curve results in a stable graph as shown in FIG. 15 or 16 and the unsuccessful measurement respresents presents one resulting in such a graph as shown in FIG. 17, 18 or 19, and the device of this invention showed no such unssuccessful result.

Further, in order to increase the number of the successful measurments, it is most desirable to make the size of every part in FIG. 12 as follows:

$D_1 = 2.4 \phi$
$D_2 = 1.8 \phi$
$l_1 = 4.5$ mm
$l_2 = 3.0$ mm
$l_3 = 1.0$ mm
$l_4 = 0.5$ mm While the solid electrolyte galvanic cell of this invention is designed for use in an oxygen sensor of the type which is usually used for measuring the concentration of dissolved oxygen in molten iron as described hereinabove, the present invention is not intended to be limited to this application, and the device of this invention may also be used as an electric contact structure for oxygen sensors of the type used for measuring the oxygen content of molten nonferrous metals (e.g., Cu, Al, Zn, etc.) or as an electric contact structure for oxygen sensors of the type used for measuring the content of elements in molten metals other than oxygen (e.g., H, N, Al, etc.) and it is capable of ensuring a high rage of success in measurement.

What is claimed is:

1. In a device for detecting oxygen content of a molten metal having a solid electrolyte galvanic cell mounted in a quartz tube with one end of said galvanic cell projected from one end of said quartz tube, and a powder reference material placed inside said quartz tube and enclosing electrode lead means and said solid electrolyte galvanic cell whereby upon immersion into the molten metal said device generates an electromotive force proportional to a partial pressure of oxygen in said molten metal, the improvement wherein the portion of said solid electrolyte galvanic cell contacting said powder reference material is formed into a shape having at least one circumferential groove to provide an increased contact area between said solid electrolyte galvanic cell and said powder reference material and to increase holding power of said powder reference material.

2. A device according to claim 1, wherein said solid eletrolyte galvanic cell has a cylindrical shaped portion, and wherein said portion of said solid electrolyte galvanic cell contacting said powder reference material comprises a first cylindrical body portion connected to said cylindrically shaped portion of said solid electrolyte galvanic cell, said first cylindrical body portion of smaller diameter than said cylindrical shaped portion, and a second cylindrical body portion connected to said first cylindrical body portion and equal in diameter with said cylindrical shaped portion, wherein said first cylindrical body portion defines said circumferential groove.

3. A device according to claim 1, wherein said solid electrolyte galvanic cell has a cylindrical shaped portion, and wherein said solid electrolyte galvanic cell portion contacting said power reference material comprises a first cylindrical body portion connected to said cylindrically shaped portion of said galvanic cell and having a smaller diameter than said cylindrical shaped portion, and a second cylindrical body portion connected to said first cylindrical body portion and greater in diameter than said cylindrical shaped portion, wherein said first cylindrical body portion defines said circumferential groove.

4. A device according to claim 1, wherein said solid electrolyte galvanic cell has a cylindrical shaped portion, and wherein said solid electrolyte galvanic cell portion contacting said power reference material comprises a first cylindrical body portion connected to a cylindrical shaped portion of said galvanic cell and having a smaller diameter than said cylindrical shaped portion, and a second cylindrical body portion connected to said first cylindrical body portion and smaller in diameter than said cylindrical shaped portion, wherein said first cylindrical body portion defines said circumferential groove.

5. A device according to claim 1, wherein said solid electrolyte galvanic cell has a cylindrical shaped portion, and wherein said solid electrolyte galvanic cell portion contacting said power reference material comprises a conical portion connected to said cylindrical shaped portion of said galvanic cell and a cylindrical body portion connected to said conical portion and equal in diameter to said cylindrical shaped portion, wherein said conical portion defines said circumferential groove.

6. A device according to claim 1, wherein said solid electrolyte galvanic cell has a cylindrical shaped portion, and wherein said solid electrolyte galvanic cell portion contacting said power reference material comprises a series of conical portions connected to said cylindrical shaped portion of said galvanic cell, wherein said series of conical portions define a series of circumferential grooves.

7. A device according to claim 1, wherein said solid electrolyte galvanic cell has a cylindrical shaped portion, and wherein said solid electrolyte galvanic cell portion contacting said powder reference material comprises a series of alternating cylinders, each alternate cylinder having a diameter less than its adjacent cylinder, said series connected to said cylindrical shaped portion of said galvanic cell, each said alternate cylinder defining said circumferential groove.

8. A device according to claim 1, wherein said one end of said quartz tube for mounting said solid electrolyte galvanic cell is bent inwardly.

* * * * *